United States Patent [19]

Temin et al.

[11] Patent Number: 4,650,764
[45] Date of Patent: Mar. 17, 1987

[54] HELPER CELL

[75] Inventors: Howard M. Temin, Madison, Wis.; Shinichi Watanabe, Wheaton, Md.

[73] Assignee: Wisconsin Alumni Research Foundation, Madison, Wis.

[21] Appl. No.: 593,175

[22] Filed: Mar. 26, 1984

Related U.S. Application Data

[63] Continuation-in-part of Ser. No. 484,323, Apr. 12, 1983, abandoned.

[51] Int. Cl.⁴ .................... C12N 5/00; C12N 15/00; C12N 7/04; C12R 1/91
[52] U.S. Cl. ............................. 435/240; 435/172.3; 435/91; 435/236; 435/948; 935/32; 935/71; 935/70
[58] Field of Search ............... 435/68, 70, 91, 172.3, 435/240, 236, 241, 317, 948, 239; 935/32, 34, 57, 58, 70, 71, 63, 62

[56] References Cited

U.S. PATENT DOCUMENTS 4,399,216  8/1983  Axel et al. ..................... 435/172.3
4,405,712  9/1983  Vande Woulde et al. ........... 435/70

OTHER PUBLICATIONS

Tabin et al, "Adaptation of a Retrovirus as a Eukaryotic Vector Transmitting the HSV Thymidine Kinase Gene", Molecular and Cellular Biology, 2(4) pp. 426–436 (4–1982).
Wei et al, "Construction and Isolation of a Transmissible Retrovirus Containing the Src Gene of Harvey Murine Sarcoma Virus", Journal of Virology, 39(3) pp. 935–944 (1981).
Steimer et al, "Envelope Assembly Mutant of Rouse Sarcoma Virus", Journal of Virology, 36(3), pp. 883–888 (1980).
Robbins et al, "Molecular Cloning of Integrated Simian Sarcoma Virus: Organization of Infectious DNA Clones", Proceedings of the National Academy of Sciences, 78(5) pp. 2918–2922 (1981).
O'Rear et al, "Mapping of Alterations in Noninfectious Proviruses of Spleen Necrosis Virus", Journal of Virology, 39(1) pp. 138–149 (1981).
Linial, "Transfer of Defective Avian Tumor Virus Genomes by Rous Sarcoma Virus RNA Packaging Mutant", Journal of Virology, 38(1) pp. 380–382 (1981).
Watanabe et al, "Encapsidation Sequence Required for Retrovirus Vectors", Eukaryotic Viral Vectors ed. Gluzman, Cold Spring Harbor Lab. 1982 p. 115.
Article by K. Shimotohno & H. Temin, "Formation of Infectious Progeny Virus After Insertion of Herpes Simplex Thymidine Kinase Gene Into DNA of an Avian Retrovirus", 26 Cell 67–77 (1981).
Article by H. Temin, "Structure, Variation and Synthesis of Retrovirus Long Terminal Repeat", 27 Cell 1–3 (1981).

List Continued on next page.

Primary Examiner—Charles F. Warren
Assistant Examiner—John Edward Tarcza
Attorney, Agent, or Firm—Quarles & Brady

[57] ABSTRACT

A helper cell for providing retrovirus protein which is required by a normally replication incompetent recombinant retrovirus gene sequence in order to replicate is disclosed. In one embodiment there is a eukaryotic host cell, a first retrovirus gene sequence in the cell which has a helper portion coding for a retrovirus protein and which is capable of expressing the retrovirus protein, and a defective portion which renders the gene sequence replication imcompetent. In this embodiment, there is also a second retrovirus gene sequence in the cell having a defective retrovirus portion, the defective retrovirus portion normally coding for the production of at least one retrovirus protein, a foreign protein coding portion, and a retrovirus cis portion. The second gene sequence is capable of expressing the foreign protein, and is capable of replacing the missing retrovirus protein with the retrovirus protein expressed by the first gene sequence so as to allow replication of the second gene sequence. This helper cell permits one to grow a stock of replication incompetent retrovirus capable of infecting a vertebrate with a foreign gene.

5 Claims, 9 Drawing Figures

OTHER PUBLICATIONS

Article by K. Shimotohno & H. Temin, "Loss of Intervening Sequences in Genomic Mouse Alpha Globin DNA Inserted in an Infectious Retrovirus Vector", 299 Nature 265–268 (1982).

Article by S. Watanabe & H. Temin, "Encapsidation Sequences for Spleen Necrosis Virus, An Avian Retrovirus, are Between the 5' Long Terminal Repeat and the Start of the Gag Gene", 79 Proc. Nat'l. Acad. Sci., USA 5986–5990 (1982).

Article by J. O'Rear et al, "Infectious and Noninfectious Recombinant Clones of the Provirus of SNV Differ in Cellular DNA and are Apparently the Same in Viral DNA", 20 Cell 423–430 (1980).

Article by I. Chen et al, "Characterization of Reticuleondotheliosis Virus Stain T DNA and Isolation of a Novel Variant of Reticuleondotheliosis Virus Strain T by Molecular Cloning", 40 J. Virol 800–811 (1981).

Article by P. Southern and P. Berg, "Mammalian Cell Transformation with SV40 Hybrid Plasmid Vectors", Eukaryotic Viral Vectors, pp. 41–45 (Cold Spring Harbor Laboratory 1982).

Article by J. O'Rear and H. Temin, "Spontaneous Changes in Nucleotide Sequence in Provirus of Spleen Necrosis Virus, an Avian Retrovirus", 79 Proc. Nat'l. Acad. Sci., USA pp. 1230–1234 (1982).

Article by Y. Gluzman, "SV40 Transformed Simian Cells Support the Replication of Early SV40 Mutants", 23 Cell 175–182 (1981).

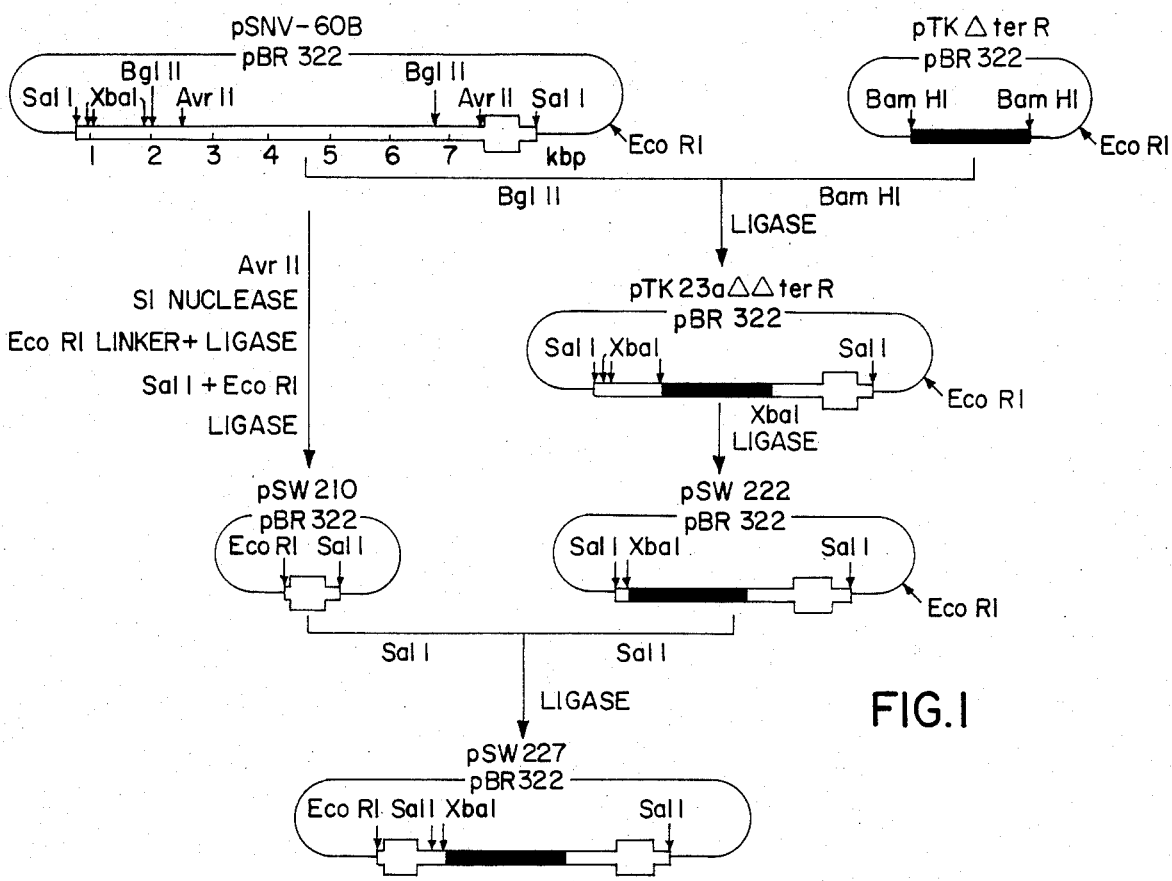
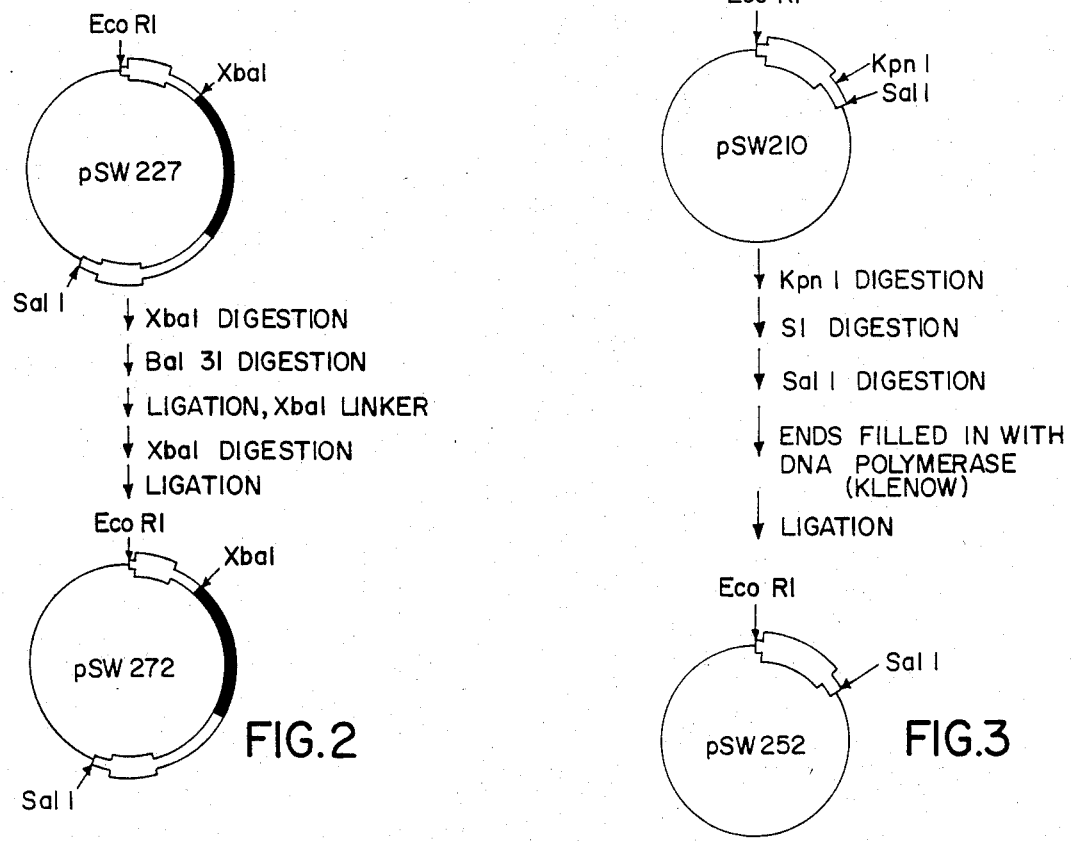
FIG.1
FIG.2
FIG.3

VIRAL RNA r pbs            CODING SEQUENCES           ppt    rAn 0.4                                                                                    8.2kb

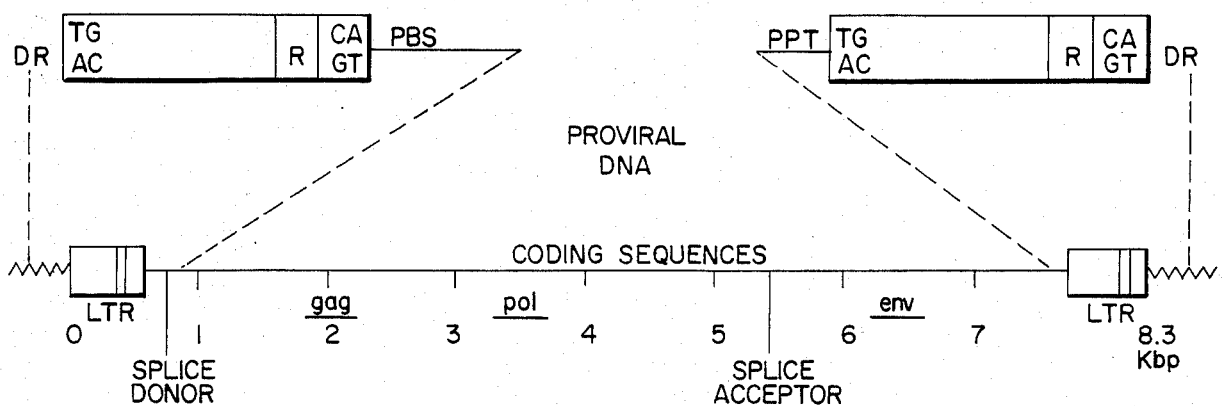
FIG. 7
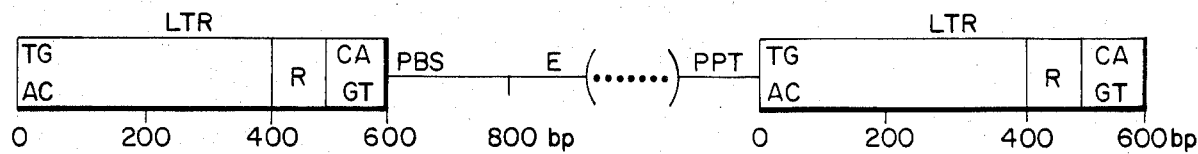
FIG. 8
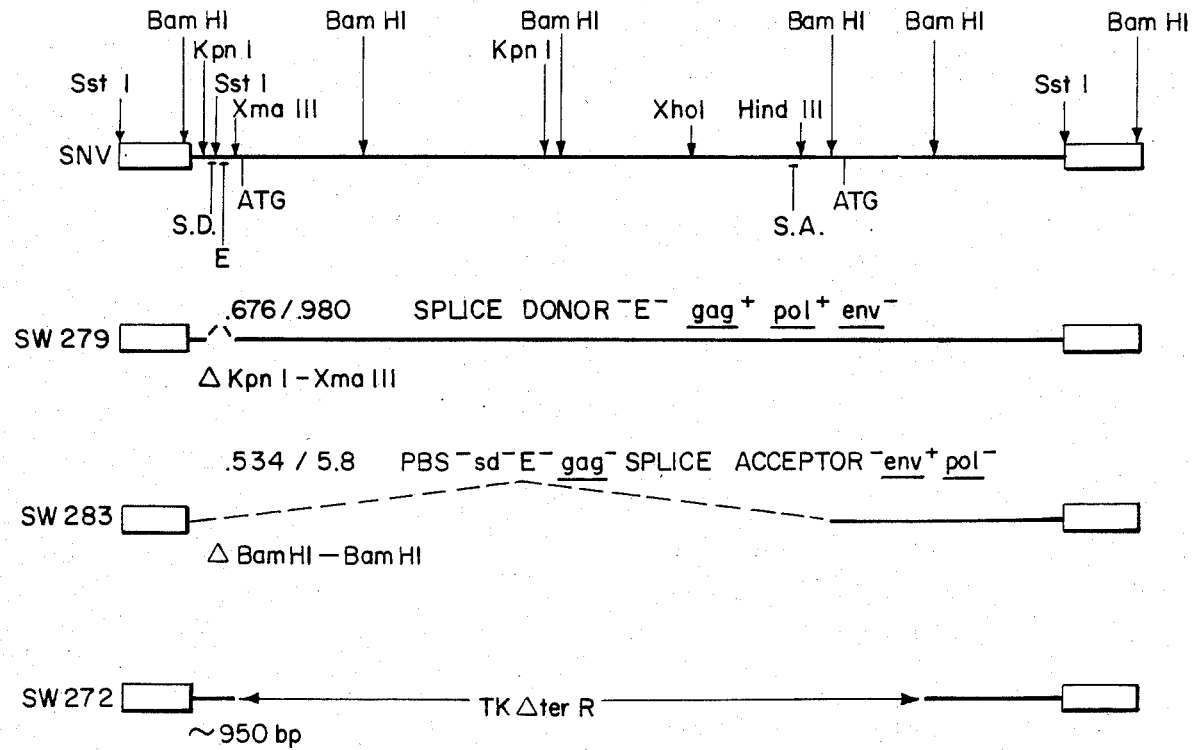

HELPER CELL

This invention was made with Government support under NIH Grant Nos. P01 CA 22443, P30 CA0 7175 and T32 CA0 9075 awarded by the Department of Health and Human Services. The Government has certain rights in this invention.

This application is a continuation in part of application Ser. No. 484,323 filed Apr. 12, 1983, now abandoned.

BACKGROUND OF THE INVENTION

A. Field of the Invention

The present invention relates to recombinant DNA technology. It is especially useful in allowing the introduction of foreign DNA into eukaryotic cells.

B. Description of the Art

There has been much interest in introducing foreign DNA into eukaryotic cells. One reaason for this interest is that some genetically caused diseases may be curable by introducing the foreign DNA into the cells, and allowing the foreign DNA to express a protein that the genetically defective cell cannot express. Another reason for this interest is that certain eukaryotic cells may prove to be the most suitable hosts for the production of certain eukaryotic proteins.

A very promising approach for achieving the introduction of foreign DNA into eukaryotic cells was disclosed in the article by K. Shimotohno and H. Temin, *Formation Of Infectious Progeny Virus After Insertion Of Herpes Simplex Thymidine Kinase Gene Into DNA Of An Avian Retrovirus*, 26 Cell 67-77 (1981). (The disclosure of this article and of all other articles cited in this application are incorporated by reference herein as if fully set forth).

This approach used retrovirus vectors for introducing foreign DNA into the vertebrate cell genome. Retroviruses are a family of RNA-containing viruses that replicate through a DNA intermediate. See generally H. Temin, *Structure, Variation & Synthesis Of Retrovirus Long Terminal Repeat*, 27 Cell 1-3 (1981)

In a normal life cycle, retroviruses integrate their DNA into the cell genome. It was discovered that it was possible to introduce the thymidine kinase (TK) gene of the herpes simplex virus type 1 into a retrovirus (spleen necrosis virus, SNV), propagate the recombinant virus to give an infectious virus, and then introduce the recombinant virus containing the foreign DNA into the cell genome. Through further research, it was discovered that other selected foreign genes (in addition to TK) could be inserted in a retrovirus vector. See K. Shimotohno and H. Temin, *Loss Of Intervening Sequences In Genomic Mouse Alpha-Globin DNA Inserted In An Infectious Retrovirus Vector*, 299 Nature 265-268 (1982).

However, in order to propagate a commercial quantity of recombinant retrovirus using this approach, one either had to construct the vector so as to make the virus replication competent, or one had to co-transfect the host cell where the virus was to be grown with a replication competent virus. Where the vector produces a replication competent virus, the resulting active virus will not be suitable for certain uses such as the introduction of the virus into a human body. If a replication competent virus is used for co-transfection, one must then be able to separate the two viruses after growth so as not to infect the human host with the second live virus after the stock has been produced. No satisfactory separation techniques are known to achieve this separation.

Thus, it can be seen that a need has existed for a relatively inexpensive way of producing a commercial size stock of replication incompetent retrovirus which contains a foreign gene and which is not contaminated by a replication competent second virus.

SUMMARY OF THE INVENTION

One embodiment of the present invention is a helper cell for providing retrovirus protein which is required by a normally replication incompetent recombinant retrovirus gene sequence in order to replicate. There is a host cell, a first retrovirus gene sequence in the cell which has a helper portion coding for a retrovirus protein and which is capable of expressing the retrovirus protein, and a defective portion which renders the gene sequence replication incompetent. Preferably, the host cell is eukaryotic, and the defective portion is in the cis portion of the gene sequence. In an especially preferred form, the defective portion codes for encapsidation.

A second retrovirus gene sequence can also be introduced into the cell. It has a defective retrovirus portion, the defective retrovirus portion normally coding for the production of at least one retrovirus protein, a foreign protein coding portion, and a retrovirus cis portion. The second gene sequence is capable of expressing the foreign protein, and is capable of replacing the missing retrovirus protein with the retrovirus protein that is expressed by the first gene sequence so as to allow the replication of the second gene sequence.

Another aspect of the invention is that the defective portions of the first and second gene sequences are positioned along the gene sequences such that the first and second gene sequences will not recombine to form a replication competent virus.

In yet another embodiment, the helper cell comprises a eukaryotic host cell, a first retrovirus gene sequence in the cell having a defective cis portion, and a partially defective helper portion which is capable of expressing at least one retrovirus protein. There is also a second retrovirus gene sequence in the cell having a defective cis portion and a helper portion coding for a retrovirus protein that the defective helper portion of the first gene sequence would normally code for in nature if not defective, but cannot express.

The present invention allows one to induce the replication of a normally replication incompetent retrovirus that contains a foreign gene of interest. A stock of the retrovirus can therefore be produced in a laboratory. However, only retrovirus containing the foreign gene will be produced by the helper cell. Also, once the virus is removed from the helper cell, the virus is then replication incompetent. The resulting retrovirus can then be used to infect eukaryotic cells (e.g. humans) without risking exposure to a replicating virus.

The selection of the encapsidation sequence as the preferred defective cis sequence for the helper gene is due to the fact that other cis control mechanisms which are involved at an earlier stage in replication may also be involved in the expression of the retrovirus protein which the vector of interest needs, while other cis portions which act after encapsidation has occurred may allow the protein to become unusable by the vector or permit the helper to replicate.

The objects of the invention therefore include:

(a) providing a helper cell of the above kind which can be used to produce a stock of replication incompetent retrovirus that carries a foreign gene sequence;

(b) providing a helper cell of the above kind which allows one to inexpensively produce a stock of replication incompetent retrovirus which is not contaminated with replication competent retrovirus;

(c) providing a helper cell of the above kind which allows one to express foreign genes in eukaryotic cells without infecting the cell with replication competent virus.

These and still other objects and advantages of the present invention will be apparent from the description which follows. In the description, the preferred embodiments of the invention will be described with reference to the accompanying drawings. These embodiments do not represent the full scope of the invention. Rather, the invention may be employed in other embodiments. Reference should therefore be made to the claims to interpret the breadth of the invention.

BRIEF DESCRIPTION OF THE DRAWINGS

FIG. 1 depicts in schematic form the synthesis of starting materials pSW210 and pSW227 from known plasmids;

FIG. 2 depicts in schematic form the synthesis of plasmid pSW272, the retrovirus vector carrying the foreign TK gene, from pSW227;

FIG. 3 depicts in schematic form the synthesis of an intermediate, pSW252, from pSW210;

FIG. 7 is a schematic view of the same section, but in proviral DNA form;

FIG. 8 is a schematic view of proviral DNA into which has been inserted a foreign gene; and FIG. 9 is a schematic view comparing a section of the SNV gene, pSW279, pSW283 and pSW272.

DESCRIPTION OF THE PREFERRED EMBODIMENTS

Figure 4:
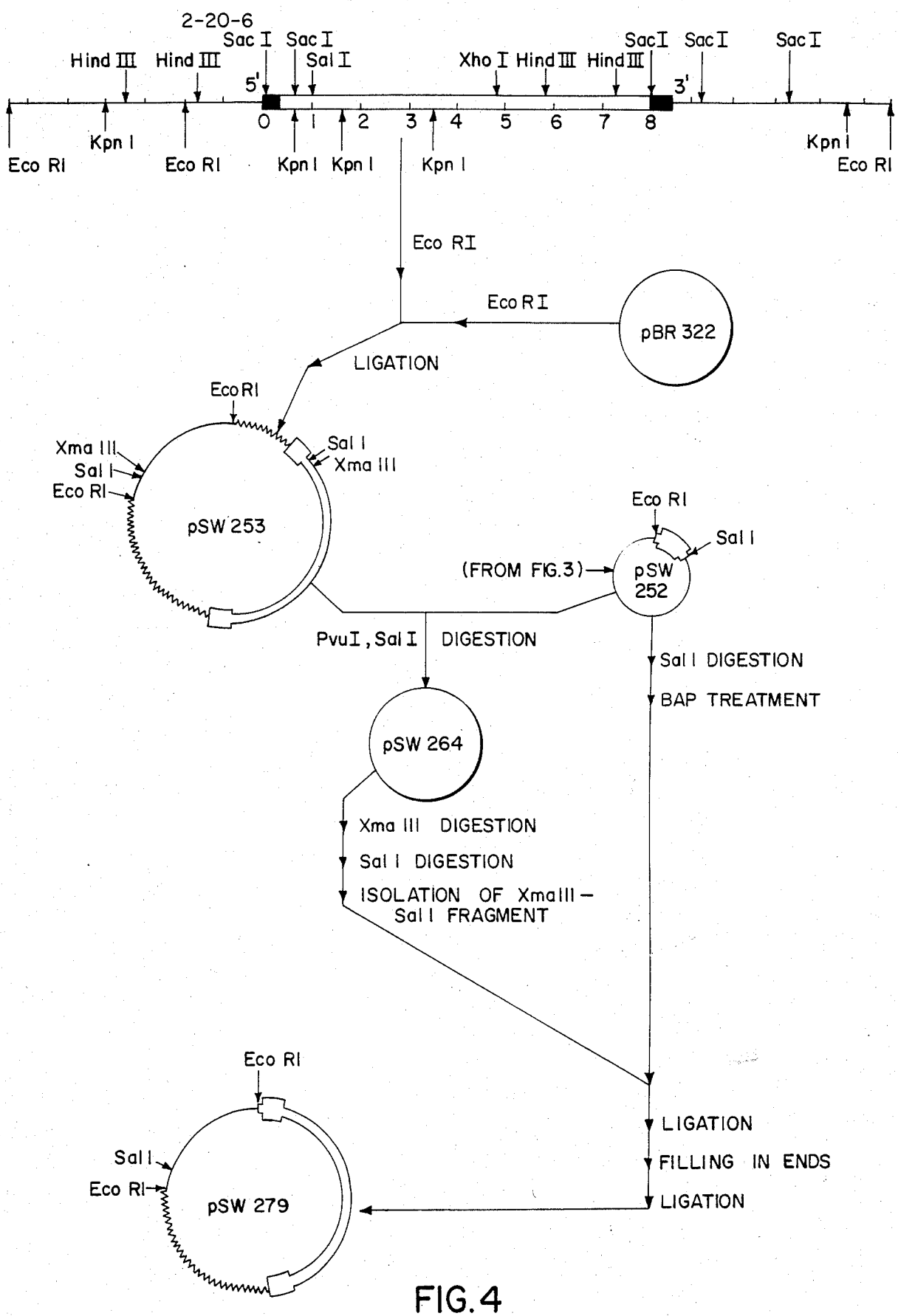
FIG. 4 depicts in schematic form the synthesis of pSW279, which contains a helper gene sequence, from a known clone and two plasmids.

The discussion below will cover the synthesis of a retrovirus vector containing the foreign TK gene of interest (pSW272), the selection of the host cell (D17 dog cells), and the synthesis of two complementary helper gene sequences, in plasmid vectors (pSW279 and pSW283).

Synthesis Of pSW272

FIGS. 1 and 2 depict the synthesis of pSW272 from pSW227, and also the synthesis of pSW227 from two known plasmids. In FIG. 1, the open bars indicate SNV sequences, the large boxes indicate LTR, and the closed boxes indicate the TK gene sequences. The single lines indicate pBR322 sequences (pBR322 in the drawings is not drawn to scale). The synthesis of pSW227 from the two known plasmids is described in detail in S. Watanabe & H. Temin, *Encapsidation Sequences For Spleen Necrosis Virus, An Avian Retrovirus, Are Between The 5' Long Terminal Repeat And The Start Of The Gag Gene*, 79 Proc. Natl. Acad. Sci. USA 5986–5990 (October 1982).

As described in that article, pSW227 is made from pSNV-60 B and pTK-delta-terR. The latter plasmid is the plasmid containing the herpes simplex virus type 1 thymidine kinase gene of interest. Its synthesis is described in K. Shimotohno and H. Temin, *Formation Of Infectious Progeny Virus After Insertion Of Herpes Simplex Thymidine Kinase Gene Into DNA Of An Avian Retrovirus*, 26 Cell. 67–77 (1981) (see especially FIG. 9 of that article).

The synthesis of pSNV-60B is described both in the 79 Proc. Natl. Acad. Sci. USA, 5986–5990 article, and J. O'Rear et al, *Infectious And Non-Infectious Recombinant Clones Of The Provirus Of SNV Differ In Cellular DNA And Are Apparently The Same In Viral DNA*, 20 Cell 423–430 (1980).

As shown in FIG. 2, once one has pSW227 one takes 10 (ug) of pSW227 and digests it with XbaI, treated with Bal 31, for 1, 2 or 3 minutes. XbaI linkers are then ligated to the ends, and the colonies are isolated and mapped using standard techniques.

Selection Of The Host

D17 dog cells (which are available from ATCC) were chosen as the host eukaryotic cell.

Synthesis Of Plasmid SW279

As shown in FIGS. 3 and 4, pSW279, one of the helper plasmids, is made from pSW264 and pSW252. pSW264 is made from pSW252 and pSW253. FIG. 3 depicts how to synthesize pSW252 from pSW210. (See FIG. 1 for synthesis of pSW210). See also S. Watanabe and H. Temin, *Encapsidation Sequences For Spleen Necrosis Virus, An Avian Retrovirus, Are Between The 5' Long Terminal Repeat And The Start Of The Gag Gene*, 79 Proc. Natl. Acad. Sci. USA 5986-5 (1982) (showing synthesis of pSW210).

pSW253 is derived from clone 2-20-6, the synthesis of which is described in I. Chen et al, *Characterization Of Reticuloendotheliosis Virus Strain T DNA And Isolation Of A Novel Variant Of Reticuloendotheliosis Virus Strain T By Molecular Cloning*, 40 J. Virol. 800–811 (1981). To produce pSW253 from clone 2-20-6, one digests the clone 2-20-6 with EcoRI at 37° C. degrees for three hours, and ligates with T4 overnight with pBR322 that has been digested with EcoRI. The resulting plasmid pSW253 is depicted on FIG. 4.

Once one has the pSW253 and pSW210 starting materials, one is then ready to produce the helper DNA (pSW279) which will supply the gag and pol retrovirus proteins, but will have a defective encapsidation (E) site. pSW210 DNA (1 ug) was digested with Kpn I at 37° C. for three hours, and treated with S1 nuclease for one hour at room temperature. After phenol extraction, DNA was digested with Sal I at 37° C. for three hours, ends were filled in with large fragment of DNA polymerase I for one hour at 14° C. and DNA was ligated with T4 DNA ligase overnight at 14° C. to give pSW252. (See FIG. 3).

pSW252 (1 ug) was digested with Sal I for three hours at 37° C., treated with bacterial alkaline phosphates for one hour at 65° C., and extracted with phenol and ethanol precipitated.

Intermediate pSW264 must then be prepared. To prepare pSW264, pSW253 (1 ug) and pSW252 (1 ug) were digested with Sal I and PvuI for three hours at 37° C., and ethanol precipitated and ligated overnight. pSW264 was then isolated.

As shown in FIG. 4, pSW264 (8 ug) was then digested with XmaIII for five hours at room temperature and ethanol precipitated. The DNA was then digested with Sal I at 37° C. for two hours, and the large fragment was isolated, mixed with the Sal I digested pSW252, and ligated overnight. The other end was filled in with the large fragment of the DNA polymerase I and ligated overnight, and the pSW279 was isolated.

Figures 5, 6:
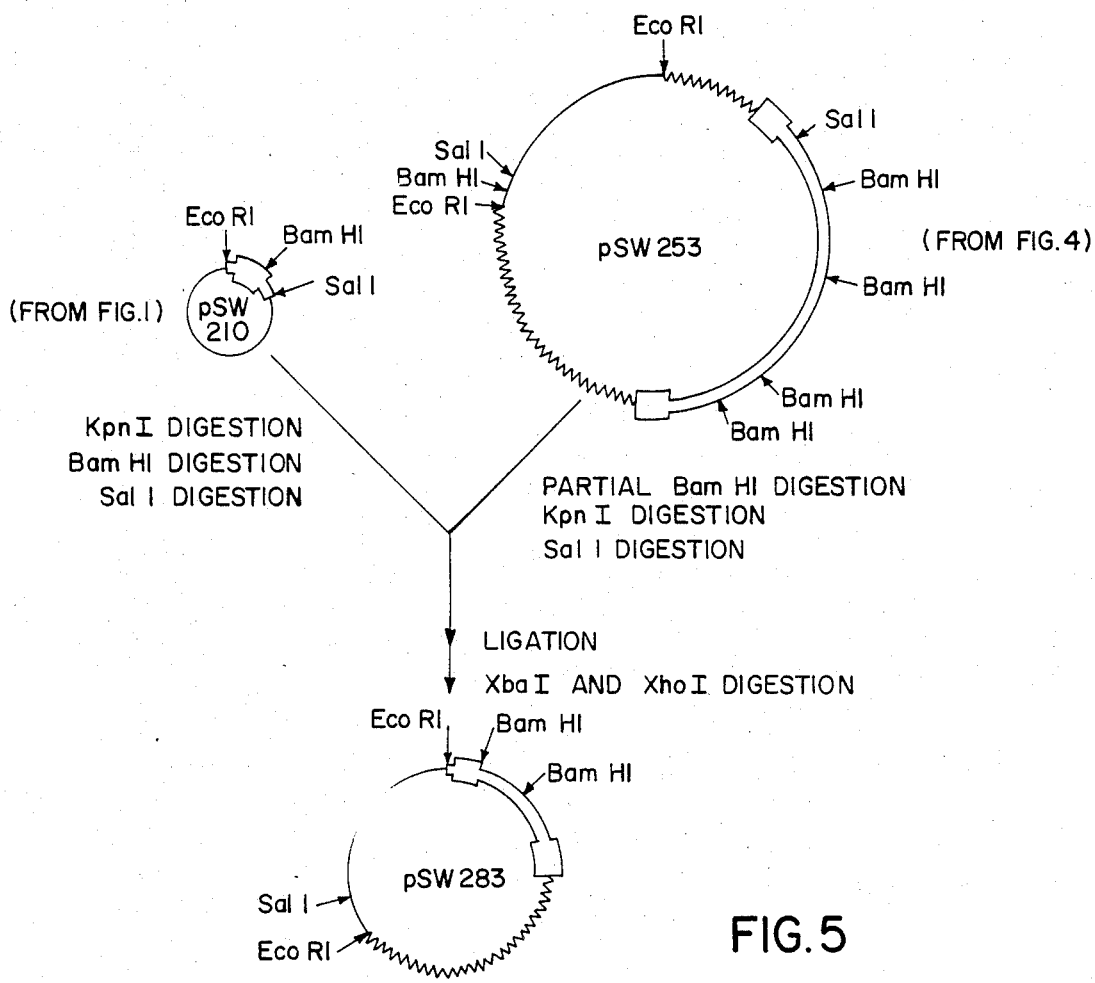
FIG. 5 depicts in schematic form the synthesis of pSW283, which contains another helper gene sequence, from two plasmids.
FIG. 6 is a schematic view of a SNV viral RNA.

Synthesis Of pSW283 pSW283 contains a second helper sequence which codes for the envelope protein (env), but is missing gag and pol coding. As shown in FIG. 5, it is made from pSW210 and pSW253 (the synthesis of both of which has previously been described). pSW253 (10 ug) was partially digested with Bam-HI and ethanol precipitated. The DNA was then digested with Kpn I at 37° C. for three hours, and then digested with Sal I for two hours at 37° C. pSW210 (2.5 ug) was digested with Kpn I for 1.5 hours at 37° C., and then digested with Bam HI and Sal I for two hours at 37° C. The DNAs were ethanol precipitated, mixed, and ligated together overnight and ethanol-precipitated. The DNA was then digested with Xba I and Xho I for two hours at 37° C., and pSW283 was isolated.

Synthesis Of The Helper Cell

Once the helper plasmids pSW283 and pSW279 were made, the D17 dog cells were transfected with 0.5 ml of a mixture of pSW283 (10 ug/ml), pSW279 (10 ug/ml), and pSV2-neo® (3.75 ug/ml) (Bethesda Research Labs). The techniques for transfection have been described in the previously cited 26 Cell article on page 75. Note, however, that the D17 dog cells are used in place of chicken, mouse or rat cells, and no special carrier is required.

pSV2-neo® is a marker that has previously been described in an article by P. Southern and P. Berg, *Mammalian Cell Transformation With SV40 Hybrid Plasmid Vectors*, Eukaryotic Viral Vectors, pp. 41–45 (Cold Spring Laboratory 1982). Transfected cells were selected with G418 antibiotic (Gibco) (400 ug/ml) which is an antibiotic which will kill cells not containing the pSV2-neo®. The surviving clones are very likely to have also picked up the pSW283 and pSW279. The clones were characterized by extracting DNA, digesting with SstI, and analyzing with Southern hybridization for the presence of DNA of pSW279 and pSW283.

Having created the supply source for the protein, the cells are then also transfected with pSW272 (10 ug/ml) (using the same transfection procedures). The resulting infectious SNV-TK was assayed on BRL-TK− cells. See K. Shimotohno and H. Temin, *Formation Of Infectious Progeny Virus After Insertion Of Herpes Simplex Thymidine Kinase Gene Into DNA Of An Avian Retrovirus*, 26 Cell. 67–77 (1981) (assay techniques).

A stock of retrovirus containing the TK gene can then be produced because the pSW279 expressess two of the necessary proteins (gag, pol), and the pSW283 expresses the env protein. None of these can be produced by the pSW272 itself. Thus, pSW272 is replication incompetent.

A deposit of the canine cells having pSW279, pSW283 and pSV2-neo® is deposited with ATCC number CRL8468, and a deposit of *Escherichia coli* having pSW272 is deposited with ATCC number 39609, and samples of both are available from the permanent collection of the American Type Culture Collection of Rockville, MD to the public upon the issuance of this patent. The deposit is also available as required by foreign patent laws in countries wherein counterparts of the subject application, or its progeny may be filed. However, it should be understood that the availability of the deposits does not constitute a license to practice the subject of the invention in derogation of patent rights granted by governmental action.

The invention can be further understood by viewing FIGS. 6–9. FIG. 6 shows an SNV viral RNA sequence before recombinant modification. FIG. 7 shows the proviral sequence of the same section. From about 1000 bp to about 7000 bp is the trans portion which codes for the gag pol and env proteins. There is also a splice acceptor between 5000 and 6000. The encapsidation function (E) is between 800 and 1000 in the cis portion of the sequence.

As shown in FIG. 8, the TK gene is inserted in the trans portion of the sequence (between the parentheses). FIG. 9 shows that pSW279 is missing only very small section of the cis portion including E, a splice donor, and subsidiary site necessary for env production FIG. 9 also shows that pSW283 has env, but not gag or pol or E. It should also be noted that the deletions on pSW283, pSW279 and pSW272 are constructed so that there can be no recombination between plasmids to produce an active virus.

It will therefore be appreciated that the present invention provides a means of controlling the replication of a retrovirus which can infect eukaryotes with a foreign gene. The retrovirus can be grown to a stock of any desired size, yet when removed from the helper cell, it will not replicate further.

As discussed above, it is expected that many types of eukaryotic genes besides the thymidine kinase gene will be appropriate for use with a retrovirus vector. Moreover, it is expected that other types of retroviruses besides SNV will prove suitable as vectors. Also, the selection of a dog cell as the preferred host is not meant to be limiting, as many other hosts may prove acceptable. As such, the invention should not be limited by the illustrative embodiments described above. Instead the invention is to be judged by the claims which follows.

We claim:

1. A helper cell, comprising:
   a host cell;
   a first retrovirus helper gene sequence in the cell which has a helper portion coding for a retrovirus virion protein and which is capable of expressing the virion protein, and a defective encapsidation portion which renders the cell by itself unable to form the infectious virus which the first retrovirus helper gene sequence codes for;
   a second retrovirus helped gene sequence in the cell having a defective helped portion which would have rendered the cell unable to form the infectious virus which the second retrovirus helped gene sequence codes for if suitable virion protein had not been supplied from expression of the first retrovirus helper portion or from another source; and
   said second retrovirus helped gene sequence being a recombinant retrovirus sequence with a first part that is retrovirus and a second part that is a foreign gene protein coding part;
   whereby the virion protein expressed by the first helper portion can permit the second retrovirus helped gene sequence to form infectious recombinant virus coding for the foreign gene.

2. The helper cell of claim 1, wherein the foreign gene is eukaryotic.

3. The helper cell of claim 2, wherein the foreign gene is a human gene.

4. The helper cell of claim 1, wherein the defective helper and helped portions are positioned along their respective gene sequences such that the first retrovirus helper gene sequence and the second retrovirus helped gene sequence will not recombine to form a single gene sequence capable of forming a complete infectious virus.

5. The helper cell of claim 1, wherein the first and second retrovirus gene sequences are not attached to each other in the cell.

* * * * *